United States Patent [19]

Clare et al.

[11] Patent Number: 5,295,482
[45] Date of Patent: Mar. 22, 1994

[54] LARGE SURFACE AREA ELECTRODE

[75] Inventors: Christopher R. Clare, Los Altos Hills; Mir A. Imran, Palo Alto; Donald E. Barnett, Jr., Sunnyvale; Albert J. Highe, Redwood City, all of Calif.

[73] Assignee: Physiometrix, Inc., Sunnyvale, Calif.

[21] Appl. No.: 964,917

[22] Filed: Oct. 22, 1992

[51] Int. Cl.$^5$ .............................. A61B 5/04
[52] U.S. Cl. ................... 128/639; 607/142
[58] Field of Search ................. 128/639–641, 128/798, 799, 802, 644; 602/2; 606/34, 41, 32–34; 607/62, 149, 152

[56] References Cited

U.S. PATENT DOCUMENTS

| | | | |
|---|---|---|---|
| 4,419,998 | 12/1983 | Heath | 128/639 |
| 4,494,552 | 1/1985 | Heath | 128/696 |
| 4,674,511 | 6/1987 | Cartmell | 128/640 |
| 4,834,103 | 5/1989 | Heath | 128/798 |
| 4,848,345 | 7/1989 | Zenkich | 128/419 |
| 4,850,356 | 7/1989 | Heath | 128/419 |
| 4,895,169 | 1/1990 | Heath | 128/798 |
| 5,063,932 | 11/1991 | Dahl et al. | 128/639 |
| 5,095,916 | 5/1992 | Smits | 128/644 |
| 5,114,424 | 5/1992 | Hagen et al. | 128/798 |

FOREIGN PATENT DOCUMENTS 1219642  3/1987  Canada ............... 326/17.3

OTHER PUBLICATIONS

Richard E. Kerber, MD, External Defibrillation: New Technologies, *Annals of Emergency Medicine*, Sep. 1984 (Part 2), 13:9, pp. 794–796.

M. Aubry-Frize, Y. Poussart, Modelling of thermal patterns of electrosurgical dispersive electrodes, Med. & Biol. Engineering & Computing, May 1986, pp. 311–315.

Stults et al., Self-Adhesive Monitor/Defibrillation Pads Improve Prehospital Defibrillation Success, *Annals of Emergency Medicine*, Aug. 1987, 16:8, pp. 872–877.

Kerber et al., Self-Adhesive Preapplied Electrode Pads for Defibrillation and Cardioversion, *JACC*, Mar. 1984, 3:3, pp. 815–820.

J. D. Wiley, J. G. Webster, Analysis and Control of the Current Distribution under Circular Dispersive Electrodes, *IEEE Transactions on Biomed. Eng.*, May 1982, 29:5, pp. 381–389.

Primary Examiner—Kyle L. Howell
Assistant Examiner—Marianne Parker
Attorney, Agent, or Firm—Flehr, Hohbach, Test, Albritton & Herbert

[57] ABSTRACT

Large surface area electrode for use with a power supply having a more uniform current density distribution for contacting the exposed surface of a living body having a contour. The electrode comprises a layer of flexible conductive material of a predetermined geometrical shape and having first and second surfaces. The layer is normally relatively flat and is capable of assuming contours of the skin of the body when the electrode is placed in contact with the body with the first surface of the layer engaging the exposed surface of the body. The layer of conductive material has a central portion and a surrounding ring portion. The central portion and the surrounding ring portion have outer margins with edges. A flexible carrier layer is provided which is secured to the second surface of the layer of flexible conductive material and serves to support the central portion and the said surrounding portion so that the surrounding portion is spaced from and insulated from the central portion. A connector is provided which is connected to the surrounding ring portion and is adapted to be coupled to the power supply for controlling the current density at the edges so that the current density at the edges does not exceed a predetermined value. The connector forms a direct connection to the central portion and includes a resistor connected to the surrounding ring.

31 Claims, 5 Drawing Sheets

FIG.12

LARGE SURFACE AREA ELECTRODE

This invention relates to large surface area electrodes.

Large area electrodes have heretofore been provided and have been utilized for applying defibrillation pulses to patients with hearts that are in defibrillation. Large area electrodes have also been used in connection with electrosurgery. In the past, in connection with such large area electrodes, it has been found that there is a concentration of current around the edges of the electrodes which creates an increased current density passing through the skin close to the edge of the electrode which causes non-uniform heating of the skin leading to increased redness of the skin in that area and possibly actual burning to the extent of causing second or third degree burns and blisters around the edges of the electrode. In addition, in some applications of large area electrodes in which the large area electrodes must be placed on the patient's skin for relatively long periods of time, there is a tendency for the electrodes to dry out and therefore substantially decrease their effectiveness. There is therefore a need for a new and improved large area electrode which will overcome these disadvantages.

In general, it is an object of the present invention to provide a large surface area electrode which has a more uniform current distribution.

Another object of the invention is to provide an electrode of the above character which will perform reliably for long periods of time.

Another object of the invention is to provide an electrode of the above character in which the current is distributed over at least one additional edge.

Another object of the invention is to provide an electrode of the above character in which the current is distributed over a plurality of edges.

Another object of the invention is to provide an electrode of the above character comprised of a plurality of separate conductive elements.

Another object of the invention is to provide an electrode of the above character which has a central conductive element and outer conductive elements.

Another object of the invention is to provide an electrode of the above character in which the conductive elements are separately connected to a power supply.

Another object of the invention is to provide an electrode of the above character in which resistors are provided for connecting the outer conductive elements to the power supply and the central conductive element is directly connected to the power supply without the use of a resistor.

Another object of the invention is to provide an electrode of the above character in which the resistors have been selected to provide a more uniform current density distribution.

Another object of the invention is to provide an electrode of the above character in which a conductive material is provided over each of the conductive elements.

Another object of the invention is to provide an electrode of the above character in which the conductive material on the conductive elements is to provide a conductive material which has a low resistivity.

Another object of the invention is to provide an electrode of the above character in which the conductive material in each conductive element is insulated from another conductive element.

Another object of the invention is to provide an electrode of the above character in which resistances are provided and adjusted so that the current distribution at the edges is generally uniform.

Another object of the invention is to provide an electrode of the above character which is conformable to the skin of a patient.

Another object of the invention is to provide an electrode of the above character in which radially extending slits are provided in the electrode to achieve improved conformability.

Another object of the invention is to provide an electrode of the above character in which the slits are provided in two sets of circumferentially spaced apart, radially extending slits with one set being offset with respect to the other to maintain good conductivity in the electrode.

Another object of the invention is to provide an electrode of the above character in which a backing material is provided for the conductive electrode and wherein the backing material is provided with circumferentially spaced apart cutouts to provide improved conformability.

Another object of the invention is to provide an electrode of the above character in which the cutouts extend through the backing material and are triangularly-shaped with their apexes facing inwardly toward the center of the electrode.

Another object of the invention is to provide an electrode of the above character in which the resistors for the electrodes are carried by connectors connected to the electrodes.

Another object of the invention is to provide an electrode of the above character in which the conductive elements have substantially equal areas.

Another object of the invention is to provide an electrode of the above character in which the conductive elements can have non-equal areas.

Another object of the invention is to provide an electrode of the above character which can be readily and economically fabricated.

Another object of the invention is to provide an electrode of the above character which can be readily applied to the patient.

Additional objects and features of the invention will appear from the following description in which the preferred embodiments are set forth in detail in conjunction with the accompanying drawings.

In general, the large surface area electrode with a more uniform current distribution is utilized for contacting the smooth surface of the skin of a living body having a contour. The electrode is comprised of a layer of flexible conductive material of a predetermined geometrical shape and having first and second surface areas. The layer is normally relatively flat but is capable of assuming the contour of the portion of the body when the electrode is placed in contact with the body with the first surface engaging the exposed surface of the skin on that body. The layer of conductive material has a central portion and a surrounding ring portion. The central portion and the surrounding ring portion have outer margins with edges. Means forming a flexible carrier layer is secured to the second surface of the layer of flexible conductive material and serves to support the central portion and the surrounding ring portion so that the surrounding ring portion is spaced from and insulated from the central portion. Coupling means is provided which is adapted to couple the central portion and the surrounding ring portion to the power supply for controlling the current density at the edges so that the current density at the edges does not exceed a predetermined value. The coupling means forms a direct connection to the central portion and includes a resistor connected to said surrounding ring portion.

Figure 1:
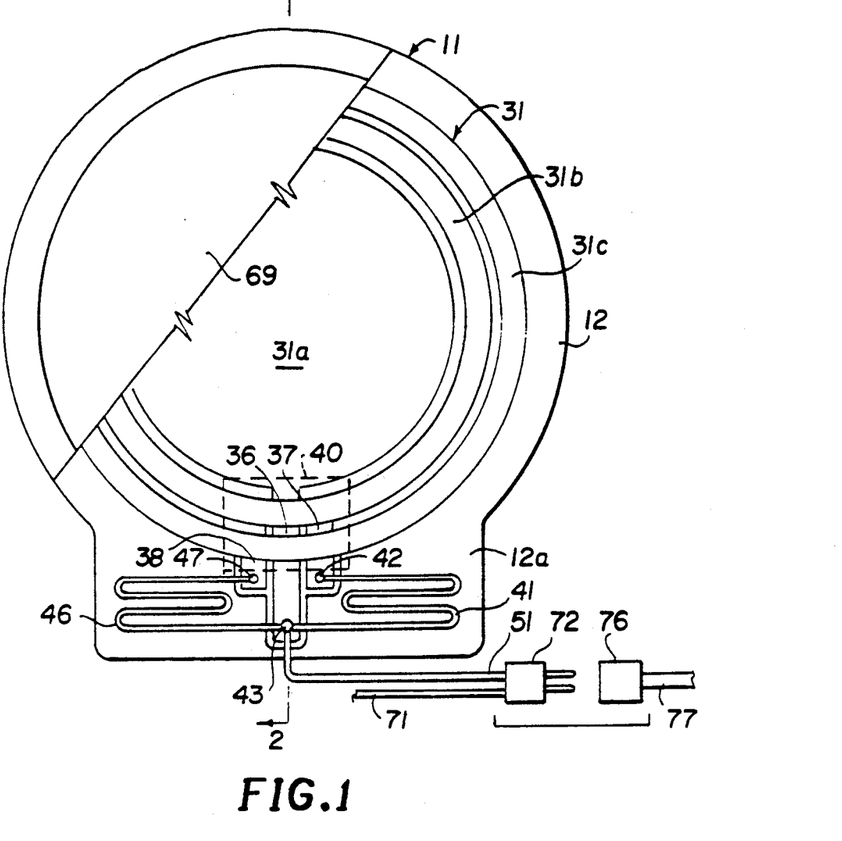
FIG. 1 is a top plan view of a large surface area electrode incorporating the present invention with certain portions thereof being removed.
Figure 2:
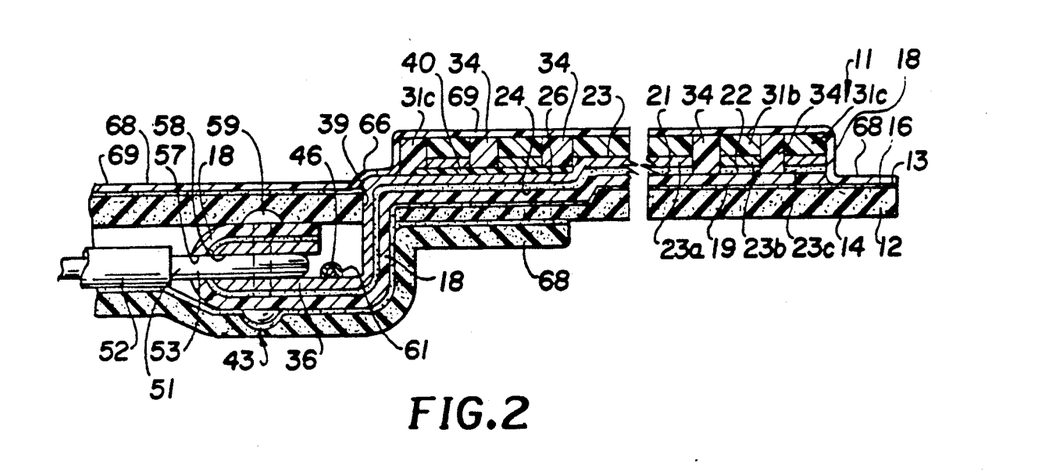
FIG. 2 is a cross-sectional view taken along the line 2—2 of FIG. 1.

More particularly, as shown in the drawings, the large surface area electrode 11, shown in FIGS. 1 and 2 of the drawings, consists of a backing or support layer 12 formed of a suitable insulating flexible material such as an adhesive closed cell soft foam having a thickness ranging approximately 0.020 inches to 0.050 inches and, preferably, a thickness of approximately 0.030 inches. The backing or support layer 12 is provided with first and second surfaces 13 and 14 upon which a suitable sticky-type adhesive 16 is present on the surface 13. The backing or support layer 12 with its adhesive 16 applied thereto can be purchased as a manufactured item and is available from a number of commercial sources. The backing or support layer 12 can have any desired geometrical configuration. For example, it can be substantially circular as shown with a tail portion 12a utilized for a purpose hereinafter described.

A carrier layer 18 is provided which can be formed of a suitable relatively strong flexible stretchable material such as a thin plastic film formed of Nylon. Alternatively, a woven plastic fabric can be provided such as one woven of Nylon. A woven carrier layer 18 may be preferable in certain applications where it is desirable to conform to a curved surface in two dimensions. In other words, it is desirable that the layer be able to stretch.

This carrier layer 18 is provided with first and second surfaces 19 and 21 with surface 19 being adherent to the adhesive layer 16 provided on the backing or support layer 12. The other or second surface 21 is provided with an adhesive 22 on the surface thereof. A conducting foil 23 having first and second surfaces 24 and 26 is provided with the surface 24 being adherent to adhesive layer 22 on the carrier layer 16. The foil 23 is in the form of a metallic conducting foil of a suitable material such as aluminum and is formed into the desired pattern in a suitable manner such as die-cutting. For example, as shown in FIG. 2 a central circular conductive foil portion or element 23a and spaced apart concentric conductive foil ring portions or elements 23b and 23c can be provided.

In accordance with the enlarged surface area desired for the electrode 11, the portions 23a, 23b and 23c can have relatively large dimensions. For example, the inner circular portion 23a can have a radius of 1.3 inches. The first ring portion 23b can have an inner radius of 1.4 inches, an outer radius of 1.7 inches. The second ring portion 23b can have an inner radius of 1.8 inches and an outer radius of 2 inches to provide a foil 23 which has an outer diameter of 4 inches. With such a construction, it can be seen that the first ring portion 23b has a width of 0.3 inches and the second ring portion 23c has a width of 0.2 inches. The adhesive backing or support layer 12 can extend a suitable distance as, for example, one additional inch beyond the outer margin of the foil 23.

A conductive elastomer layer 31 is adherent to the surface 26 of the foil 23 and is generally patterned in the same way as the foil 23 to provide a central conductive elastomer portion or member 31a and two conductive elastomer ring-like portions or members 31b and 31c. The conductive elastomer 31 is preferably of the type described in U.S. Pat. No. 5,211,714. It should be understood, however, that any elastomer such as an ionically conductive hydrogel or an electrically conductive composite can be used. The conductive elastomer 31 is characterized by its dryness and its retention tackiness over extended periods of time. As described therein, it can be comprised of a conductive silicone. The constituents of this conductive elastomer layer, as disclosed in said co-pending application, are incorporated herein by reference. This conductive elastomer will not be described in detail because of the detailed disclosure in said co-pending application.

The portions 31a, 31b and 31c of the conductive elastomer layer 31 are electrically separated from each other and are spaced apart as shown in the drawings by a suitable distance as, for example, 1/16" and are supported by the carrier layer 18 which serves as an insulator. As pointed out previously with respect to the foil layer 23, the conductive elastomer layer 31 also can have various geometric shapes as desired. The annular or circular spaces 32 and 33 provided between the portions 31a and 31b and between portions 31b and 31c can be filled with a suitable non-conducting elastomer 34 as shown in the drawings to provide a flush surface extending across the top of the conductive elastomer layer 31. The non-conductive elastomer 34 serves two functions. It serves to provide a continuous sticky surface on the top surface of the electrode 11. It also serves to prevent any migration of the relatively soft conductive elastomer layer 31 and thereby serves to maintain the spacing and concentricity of the conductive ring portions 31b and 31c.

Means is provided for making contact to the portions 31a, 31b and 31c of the conductive elastomer layer 31 and consists of leads 36, 37 and 38. The leads can be separate or can be formed integral with the foil portions 23a, 23b and 23c, as for example by die-cutting or etching the same from a single sheet of foil. The integral lead 36 extends through a hole 39 in the support layer 12 (see FIG. 2) and is electrically coupled to the portion 23a. The leads 37 and 38 also extend through the hole 39 and are electrically connected to the ring-like portions 31b and 31c in a similar manner. As can be seen, particularly in FIG. 1, the leads 36, 37 and 38 are electrically isolated from each other and extend outwardly in a generally radial direction over the tab or tail portion 12a of the support layer 12. In order to make it possible to make the conductive elastomer ring members 31b and 31c in continuous circles and bridge over the leads 36, 37 and 38, it is necessary to insulate the leads 36 and 37 from the ring members 31b and 31c. This can be accomplished by individually insulating the portions of the leads underlying the ring members 31b and 31c. Alternatively, as shown in FIGS. 1 and 2, this can be accomplished by inserting a rectangular piece in the form of an adhesive patch 40 of a suitable flexible insulating material such as a polyimide with an adhesive thereon between the three leads 36, 37 and 38 and the ring members 31b and 31c.

Resistance means is provided for connecting the leads 36, 37 and 38 to an appropriate power supply (not shown), as for example a defibrillator power supply, and for dividing the voltage applied to the conductive elastomer members 31a, 31b and 31c to achieve the desired current densities. It has been found that it is unnecessary to have a resistor for the center portion or members 31a to achieve the desired current distribution. Such resistance means thus consists of resistor 41 which is in a suitable form as, for example, a thin film resistor such as shown in FIG. 1. One end of the resistor 41 is connected to the lead 37 at 42 and the other end of the resistor 41 is connected to the lead 36 at 43. Another similar thin film resistor 46 is provided which has one end connected to the lead 38 at 47 and has the other end connected to the lead 36 at 43. The lead 36 at the connection 43 is connected to another lead 51 which extends to the outside world. This connection 43 is shown in FIG. 2 in which it can be seen that the lead 51 is covered by an insulator 52 and is connected to a connector 53. The connector 53 extends through holes 57 and 58 provided in the fold-over portion of the carrier layer 18 and the foil lead 36 so that the connector 53 is engaged on two sides by the foil lead 36 and is clamped together by a fastener 59. The resistors 41 and 46 are connected to the foil 23 by suitable means as solder 61 (see FIG. 2). Another layer 68 of the same adhesive foam utilized for the backing or support layer 12 is secured to the surface 14 of the backing or support layer 12 and overlies the electrical connection formed by the fastener 59 with the lead 51. This layer 68 serves to permit the electrodes from shorting out to each other and for preventing personnel utilizing the same from being shocked by an electrical current.

In connection with the present invention, the resistors 41 and 46 hereinbefore disclosed have been formed in a foil which has been etched into the appropriate shape to provide the appropriate resistances desired. It should, however, be appreciated that standard resistors as, for example, carbon film resistors or Nichrome wire can be utilized if desired. The use of the thin foil makes it possible to provide a low profile for the electrode 11 while still providing good power handling capabilities economically.

Although, in the present invention, the resistors 41 and 46 which have been utilized have been disclosed as being part of the electrode itself it should be appreciated that separate conductors or wires can be brought out from the ring portions or elements 21b and 21c and the resistors applied externally to achieve the same results.

A release liner 69 serving as a protective layer is provided which overlies the conductive elastomer layer 31 and has its outer margins adherent to the adhesive layer 16 of the backing or support layer 12. The release liner can also be formed of a material which is substantially moisture impervious to increase the life of the large area electrode when it is out of its packaging.

In FIG. 2, the vertical dimensions have been exaggerated to illustrate the various layers forming a part of the electrode 11. The electrode assembly shown in FIGS. 1 and 2 is in reality in the form of a relatively thin flexible sandwich. The release liner 68 remains in place until the electrode 11 is ready to be used.

Generally, the electrodes 11 are utilized in pairs and for that reason an additional lead 71 has been provided as shown in FIG. 1 which is connected to another electrode of the same type as shown in FIG. 1 with both electrodes being connected to a male connector 72 of a conventional type by the leads 51 and 71. The male connector 72 is adapted to mate with a female connector 76 which is connected by a lead 77 to a conventional power supply (not shown) hereinbefore described.

Figure 3:
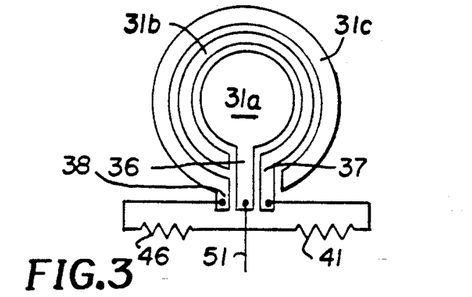
FIGS. 3 and 4 are schematic illustrations showing the manner in which resistors are connected in the electrode shown in FIG. 1.
Figure 4:
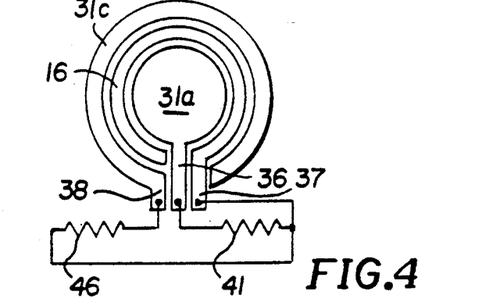

FIGS. 3 and 4 show two different arrangements showing how the resistors 41 and 46 can be utilized for interconnecting the portions 23a, 23b and 23c underlying the portions 31a, 31b and 31c of the conductive elastomer layer 31. In the arrangement shown in FIG. 3, the current carrying lead 51 is connected to the center conductor 36 connected to the circular portion 31a and with one end of each of the resistors 41 and 46 being connected to the lead 51 and the other ends of the resistors 41 and 46 being connected to the leads 37 and 38. Typically, the resistors 41 and 46 have different values with the resistor 41 connected to the inner ring portion 31b being of a smaller resistive value than the resistor 46 connected to the outer ring portion 31c.

In the arrangement shown in FIG. 4, the conductor 51 is again directly connected to the central lead 36 connected without a resistor to the portion 31a with the resistor 41 being connected from the lead 36 to the lead 37 and with the resistor 46 being connected from the lead 38 to the lead 37. In such an arrangement, the resistor 41 would be the smaller resistor whereas the resistor 46 would be the larger resistor.

It should appreciated that in accordance with the present invention it is desirable to provide at least one ring which surrounds the central portion; however, it is preferable to provide at least one additional ring. Other rings can be provided if desired. By way of example, the resistors 41 and 46 in the arrangement shown in FIG. 3 have values of approximately 10 and 25 ohms, respectively, whereas in the arrangement shown in FIG. 4, the resistors 41 and 46 would have values of 5 and 14 ohms, respectively.

Both of the arrangements shown in FIGS. 3 and 4 can be utilized. In certain applications, the arrangement shown in FIG. 4 may be desirable because it ensures that the outer electrode is always at a lower voltage than an inner electrode. It cannot possibly be higher since its driving voltage is received from the preceding inner ring.

In utilizing the electrodes incorporating the present invention in applications, for example, in applying defibrillation pulses to patients with hearts that are in fibrillation from a conventional defibrillator power supply, it has been found that the use of the concentric ring portions of a conductive elastomer greatly reduces the current concentration at the outer edges of the electrode. This greatly reduces current crowding at the surface of the skin of the patient to thereby avoid burning and substantially reduce any redness induced in the skin by the application of the defibrillation pulses. By utilizing the concentric ring portions of the present invention, it is possible to step down the voltage which is applied to the patient from the center of the electrode outwardly so that there is no more than an appropriate proportion of the voltage at each margin of the electrode to thereby control the amount of current at each edge in the electrode.

In accordance with the present invention, the voltage is adjusted so that the peak current at the outer margin or edge of each of the portions 31a, 31b and 31c is no more than a predetermined amount and, preferably, approximately equal. Typically, this is ascertained by determining the resistance values in conjunction with normal skin impedance levels. The resistors are then selected so that on an average the current flow is shared between the electrode portions 31a, 31b and 31c. In addition, it has been found desirable to tailor the area of the concentric ring portions 31b and 31c so their areas decrease the farther they are from the center of the electrode. It has been found that the same current density can be obtained on the outer margin of a smaller area outer electrode as on the outer margin from a larger area electrode disposed inwardly toward the center from the outer electrode. In fact, it has been found that the same difference in current density occurs between the outer and inner edges of two concentric ring portions as occurs between the outer edge of a circle and the center of a circle. As the area of a ring portion increases, the ratio of current density from the outer edge to the inner edge of that ring portion decreases. Thus, as the area of the ring portion increases, the current flow at the edge increases. To optimize the size of the ring portions, an area is chosen for the ring portions so that at the outer edge of the ring portions, the current density drops down to approximately the same level as it does in the center of the center electrode portion. In the next ring portion from the center its area is chosen in a similar manner until current density at the outer edges is of the same value. The farther a ring portion is from the center of the electrode, the area is decreased to obtain the same current density at the outer edge.

Figure 5:
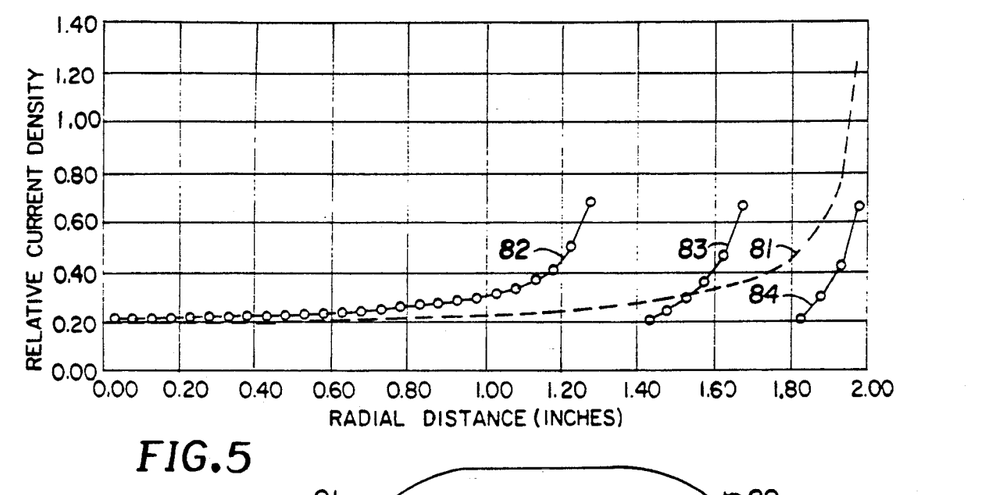
FIG. 5 is a graph showing the current distribution in the electrode shown in FIG. 1.

In this way, it is possible to keep the minimum-to-maximum current density variation which appears at any place in the large surface area of the electrode 11 in a small range to prevent current concentration at the edges which might cause burning. This is shown in graph in FIG. 5 in which the relative current density for one embodiment of the present invention having three non-equal area portions is plotted with respect to radius. The dotted line 81 shown in FIG. 5 shows a typical curve for an electrode made in accordance with the present invention but without the use of separate ring portions in which the conductive elastomer is continuous from the center to its outer margin. As can be seen from curve 81, the relative current density increases from 0.20 at the center of the electrode in a substantially straight line horizontal up to about 1.2" and thereafter progressively increases rapidly as the radial distance nears the outer margin of the electrode. The three curves 82, 83 and 84 represent the current density on each of the three portions of a three-area electrode. Curve 82 is for the center portion 31a, curve 83 is for the ring portion 31b and curve 84 is for the outer ring portion 31c.

The total current that is being delivered by the electrode is given by the integral of the product of the value represented by the curve 81 at a given radial distance and the area element of that radial distance. By going to multiple electrodes as shown in FIG. 1, it is still desirable to conserve current. By lowering current densities at the outer edges of the portions 31a, 31b and 31c, it is necessary to raise the current density elsewhere in the electrode. By examining curve 84, it can be seen that the current density has been greatly reduced in the area of the electrode exceeding 1.8 radial inches. Thus, the relative current density for curve 84 goes from approximately 0.20 to approximately 0.65, which is substantially below that of curve 81. However, the curve 83 for the portion 31c shows that while the current density starts at approximately 0.20, it goes above the curve 81 for the radial distance 1.4 to approximately 1.7 to approximately 0.65 to provide an increased relative current density with the maximum current density being approximately the same as that of the outer segment 31c as represented by curve 84. For curve 82, the relative current density starts at 0.20 at the center and then remains relatively straight or flat, the same as curve 81, but at approximately 1.1 radial inches the current density increases substantially above that of curve 81 and, again, ends up at a maximum current density of approximately 0.65, the same as for curves 83 and 84. From the three curves 82, 83 and 84, it can be seen that the maximum current density at the outer edges of the three portions 31a, 31b and 31c are substantially the same and that the minimum-to-maximum current density in each portion is also substantially the same, to thereby greatly reduce the possibility of any burning occurring at the edges during use of the electrode in defibrillation.

In utilizing the large surface electrode of the present invention, it has been found that the defibrillation threshold is equal to or better than which can be obtained with threshold defibrillator electrodes which are presently available on the market. Large single burn rings normally associated with the commercially-available electrodes have been greatly minimized or eliminated. In the present invention, a large portion of the energy which has been previously concentrated at one edge of the electrode is now distributed across the entire electrode with the concentrations at the additional edges being greatly diminished so that no burning of the skin of the patient occurs but only a slight redness appears at three concentric ring-like locations at the outer margins of the inner portion 31a, the outer margin of the concentric ring portion 31b and the outer margin of the concentric ring portion 31c. Thus, with a large surface area electrode of the present invention, the current distribution through the skin has been distributed over a larger area of the skin to greatly reduce the possibility of burning of the skin of the patient even after an exposure to a significant number of high energy pulses to the extent that only a reddening of the skin of the patient occurs with no severe burning being present. As pointed out previously, this is achieved by the use of a plurality of concentric rings in which resistors are utilized to provide voltage drops between the rings to thereby distribute the current flow to the rings.

In addition, it has been found that the large area electrodes of the present invention using the material disclosed in copending application Ser. No. 07/745,863, filed Aug. 16, 1991, are relatively transparent to x-rays and thus cast a minimum shadow when used in medical procedures. This shadow is almost invisible.

Typically, the electrodes of the present invention are sold in pairs and are used in that manner. When used, they are typically disposed of after use.

Figure 6:
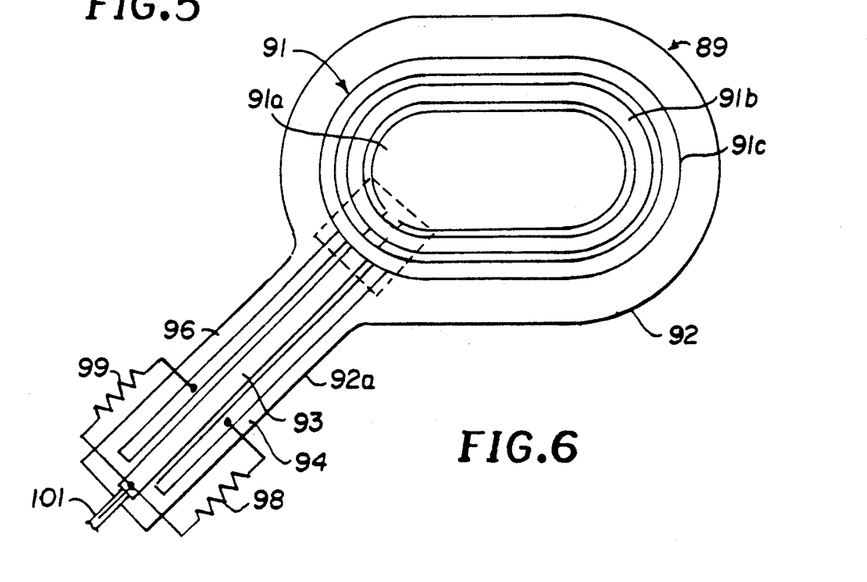
FIG. 6 is a top plan view of another embodiment of an electrode incorporating the present invention.

Another embodiment of a large surface electrode that incorporates the present invention is shown in FIG. 6 and has an oval geometrical configuration rather than the circular configuration shown in FIG. 1. This oval configuration can be envisioned as splitting the circle shown in FIG. 1 in half and moving them apart and inserting a straight portion therebetween. The oval-shaped electrode 89 is constructed in a manner similar to that shown in FIGS. 1 and 2 and includes a conductive elastomer layer 91 having a central portion 91a and surrounding portions 91b and 91c. The conductive elastomer 91 is carried by a backing or support layer 92 which is the same type as backing or support layer 12. The backing layer 92 is provided with a tail 92a which extends at approximately a 45° angle from the longitudinal axis of the oval-shaped electrode 89. Leads of the type heretofore described in connection with the previous embodiment are provided on the tail 92a and consist of a lead 93 which is connected to the central portion 91a, lead 94 connected to the portion 91b and lead 96 connected to the portion 91c. Resistors 98 and 99 are provided on the tail 92a. As shown schematically in FIG. 6, resistor 98 is connected between the conductor 93 and the conductor 94 whereas resistor 99 is connected between the conductor 93 and the conductor 96. The conductor 93 is connected by an insulated conductor 101 to a suitable connector of the type hereinbefore described such as connector 72 shown in FIG. 1.

The current distribution in the large surface area electrode 89 shown in FIG. 6 and is very similar to the current distribution for the electrode in FIG. 1. The current distribution will still be relatively uniform throughout the surface area of the electrode with a sharp decline at the edges as hereinbefore described in conjunction with the previous embodiment. The current on the curved portion of the electrode 88 will be slightly higher than the current along the straight portions of the electrode. However, the salient feature of current sharing between the electrode portions is present to the same extent in FIG. 6 as it is in FIG. 1.

In accordance with the present invention, the tail 92a should have a length of approximately 6" or longer. This makes it possible to make connections through connectors and the like to the electrode 89 outside the normal x-ray field so that the visibility of the subject matter within the body human being examined will not be occluded by shadows from the connectors and the like making connections to the electrode 89.

By use of the oval-shaped electrode, it is possible to achieve a reasonably large surface area equivalent to that which can be obtained with a circular electrode to thereby provide an equivalent defibrillation efficacy. Using such an oval-shaped electrode or pad 89 which typically would be placed over the apex of the heart of the patient with the tail extending downwardly over the side of the patient. The use of the oval-shaped electrode leaves sufficient space on the chest of the patient above the electrode 89 so that the precordial electrodes (not shown) can be appropriately placed. The large surface area circular electrodes such as that shown in FIG. 1 would make it difficult to properly place the precordial electrodes particularly on smaller patients.

Figure 7:
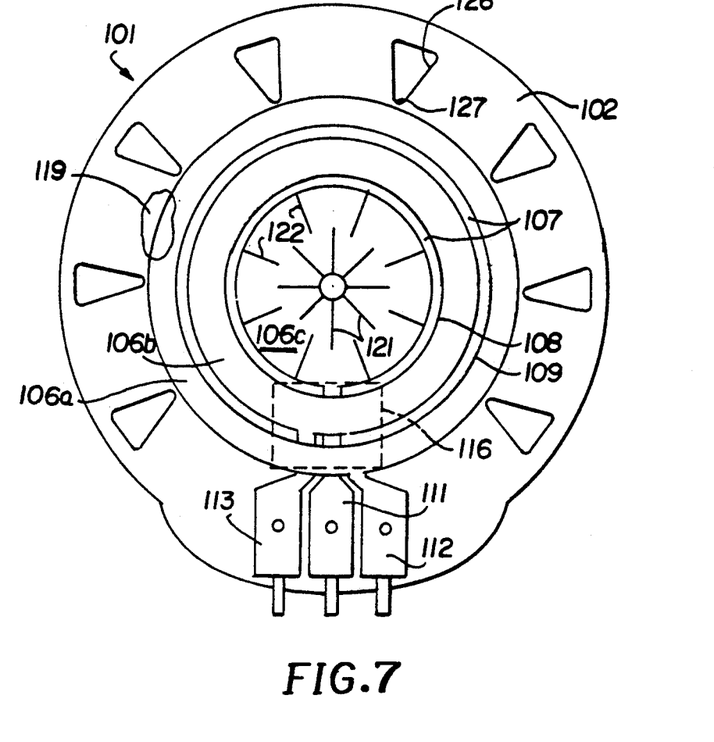
FIG. 7 is a top plan view of another embodiment of a large surface area electrode incorporating the present invention and having electrode elements of substantially equal area.

Another embodiment of a large area electrode incorporating the present invention is shown in FIG. 7. The electrode 101 is provided with a backing or support layer 102 similar to the backing or support layer 12, and is also provided with a carrier layer (not shown), a foil layer 104 over which there is disposed a layer 106 of a conductive elastomer of the type hereinbefore described. The conductive elastomer is again divided into three portions 106a, 106b and 106c, with the portion 106a being a circular central portion, portion 106b being an intermediate ring portion or member, and portion 106c being an outer ring portion or member. The portions or members 106a, 106b and 106c correspond to the portions 31a, 31b and 31c hereinbefore described in conjunction with the electrode 11 shown in FIG. 1, with the principle difference being that the portions of the conductive elastomer in FIG. 1 have unequal areas, whereas the portions 106a, 106b and 106c have substantially equal areas.

Leads 111, 112 and 113 are provided which are connected to the portions 106a, 106b and 106c, respectively. They are connected in the manner hereinbefore described in connection with the manner by which the leads 36, 37 and 38 are connected to the portions 31a, 31b and 31c. A polyimide insulating patch 116 is provided for insulating the leads 111, 112 and 113 from the continuous rings of portions 106b and 106c in the manner hereinbefore described in conjunction with FIG. 1. It should be appreciated that, if desired, the portions 106b and 106c can be provided in the form of ring segments to provide a radial space between the segments, if desired, through which the leads can extend. This would make it unnecessary to utilize the insulating patch 116.

A nonconductive elastomer 107 is provided in the annular spaces 108 and 109 provided between the portions 106a and 106b, and 106b and 106c, and serves the same purpose as the nonconductive elastomer 34 in FIG. 1. A protective release liner 119, similar to the release liner 69, is placed over the conductive elastomer 106.

It should be appreciated that the conductive elastomer 106 can be any type of conductive material. For example, it could be an ionically conductive material such as a gel or an electrolyte-filled sponge material. The insulating material between the conductive elastomer portions or rings can be any nonconducting material. As explained previously, it can be a simple elastomer or it can be a gel which has not been filled, as for example a silicone gel.

In order that the electrode 111 will conform more readily to the skin of the patient, first and second sets of slits 121 and 122, respectively, are provided in the foil 104 underlying the center conductive portion 106a. The slits 121 in the first set radiate outwardly in a radial direction from the center, and with the slits 122 of the second set of slits extending radially inwardly from the outer margin of the central electrode portion 106a. The slits 121 and 122 of the first and second sets are offset circumferentially or staggered with respect to each other. The length of the slits 121 and 122 is such so that they extend approximately one-half the radius of the center portion 106a. At least three of such slits should be provided in each set. However, additional slits can be provided, as for example the eight slits for each set which are separated by 22.5° as shown in FIG. 7. In order to impart maximum flexibility, the length of the slits should be as long as possible. However, it is necessary to retain conductivity in the metal foil 104 which underlies the conductive elastomer, and therefore it is generally desirable to only have the slits extend approximately one-half the value of the central portion of the metal foil so that good conductivity is maintained without unduly increasing the path length for current flow.

In order to impart still additional greater flexibility to the electrode, the outer margin of the backing or support layer 102 is provided with a plurality of circumferentially spaced apart, generally triangular cutouts 126 with their apices 127 facing radially inwardly to the center of the electrode 101. As can be seen, the cutouts 126 are positioned inwardly of the outer margin of the backing or support layer 102 and do not intersect the outer perimeter of the backing material. It should be appreciated that the cutouts can have configurations other than the triangular configuration shown. It is only necessary that the cutouts have more than two sides to remove some material. As in the previous embodiment, on top of the support layer 102 there is a Nylon carrier layer (not shown) upon which there is superposed the metal foil 104.

Figure 8:
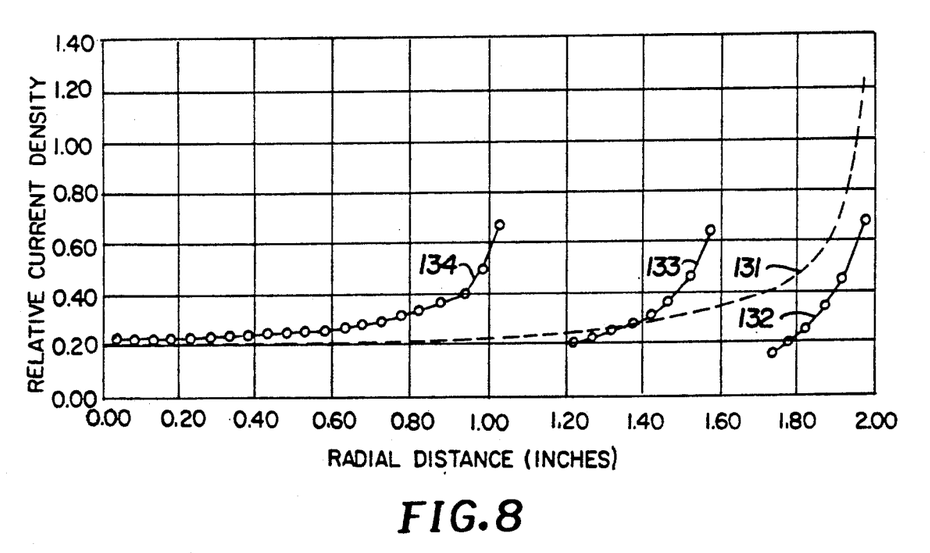
FIG. 8 is a graph showing the current density versus radial distance for the electrode shown in FIG. 7.

FIG. 8 shows a graph for the three equal-area portions provided in FIG. 7, and the relative current densities which occur. Curve 131 represents the current density for a single large area electrode, whereas the curves 132, 133 and 134 represent the current densities for the electrode portions 106c, 106b and 106a, respectively. The curves 132, 133 and 134 show that even though equal current is being supplied to each of the segments 106a, 106b and 106c, the current density on each of the segments is not the same. Comparing the curves with those shown in FIG. 5, it can be seen that the current density distribution for an electrode of non-equal areas is slightly better than an electrode which utilizes equal areas. However, both configurations provide good electrodes.

Figure 9:
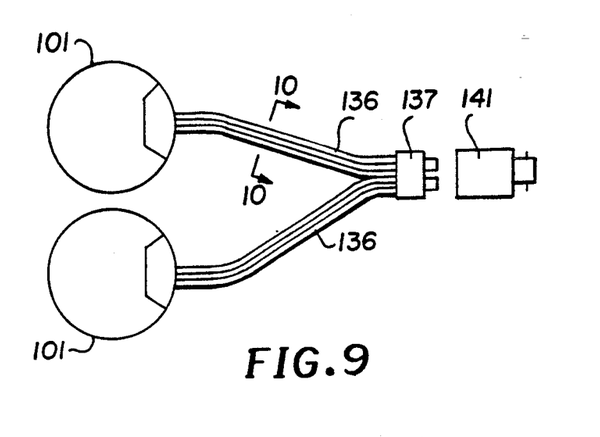
FIG. 9 is a drawing showing the manner in which a pair of electrodes incorporating the present invention is interconnected to cable adapters of an existing defibrillator or cardioverter.
Figure 10:
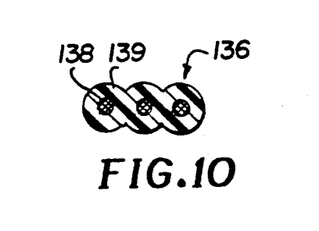
FIG. 10 is a cross-sectional view taken along the line 10—10 of FIG. 9 showing the type of cable utilized.

As explained previously, when the electrodes 11 as shown in FIG. 1 or electrodes 101 as shown in FIG. 7 are utilized for defibrillation, a pair of such pads typically are used. Thus, as shown in FIG. 9, a pair of pads of the electrodes or pads 101 are provided with one, for example, being for the left leg and the other for the right arm, and have their leads 111, 112 and 113 connected by three-wire cables 136 to a male connector 137. As can be seen from FIG. 10, the cables 136 are comprised of three separate multi-stranded conductors 138 which are arranged side-by-side and are insulated from each other by a soft elastomer 139 such as a silicone to provide a flat flexible cable. The male connector 137 is adapted to be inserted into a female cable adaptor 141 that includes within it two resistors which have been interconnected as hereinbefore described in the manner shown in FIGS. 3 or 4. Thus, there is provided the appropriate voltage and current to the electrodes 101 to provide the desired current distribution between the three portions 106a, 106b and 106c of the electrode 101. The cable adaptor 141 is connected to a cable (not shown) which can be connected to a conventional defibrillator power supply.

Figure 11:
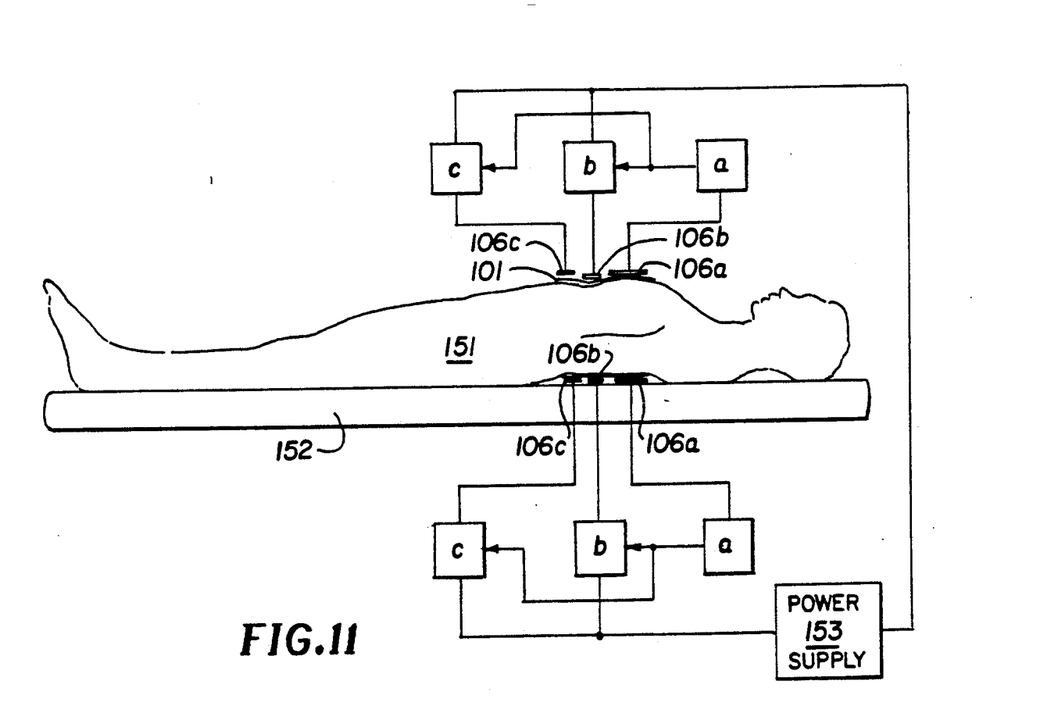
FIG. 11 is circuit diagram in block form showing the manner in which electrodes of the present invention are utilized with a patient for causing defibrillation.
Figure 12:
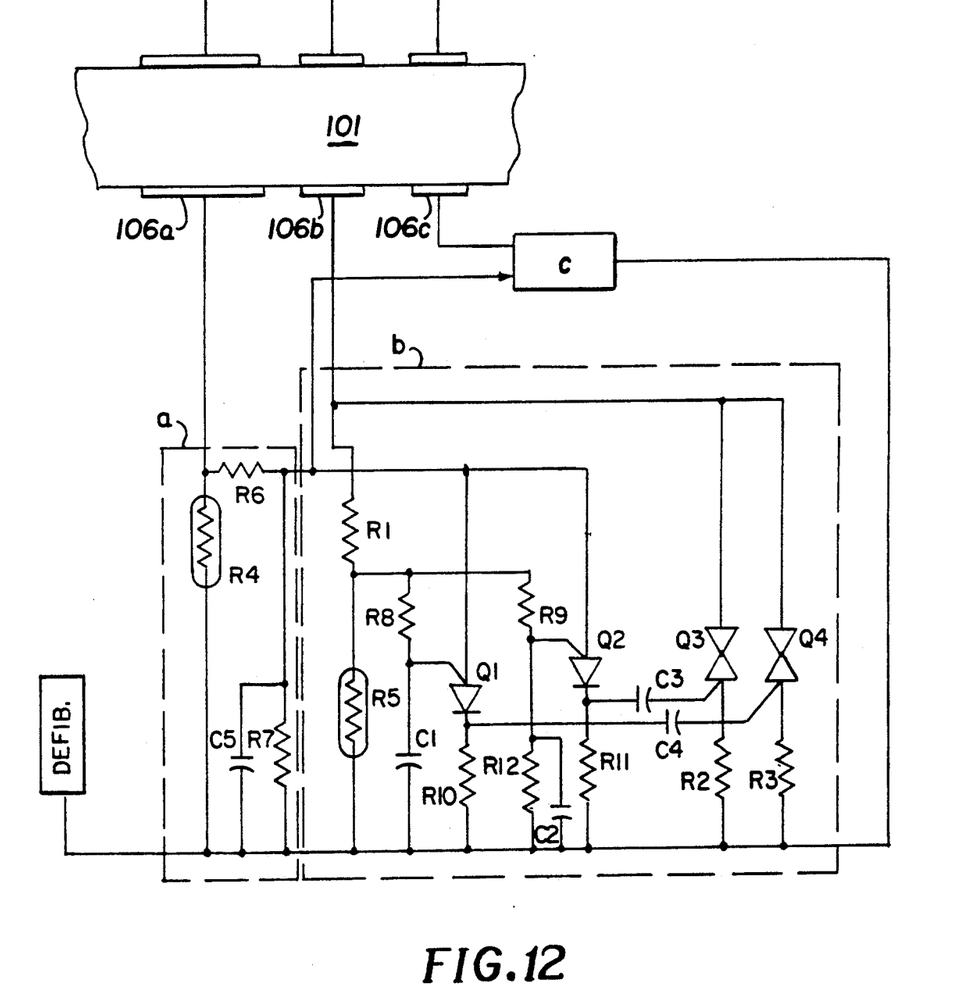
FIG. 12 is a detailed circuit diagram of a portion of the circuitry shown in block form in FIG. 11.

In connection with the present invention it has been found that the skin impedance varies from patient to patient. There can be a range of values, resulting primarily from differences between poor contact with the skin of the patient or very good contact with the skin of the patient or because of different types of skin. There is therefore a need in connection with the large area electrodes of the present invention to compensate for these differences in skin impedance so that the defibrillation current can be properly distributed between the center and the two outer rings. A block diagram of a circuit for accomplishing this result is shown in FIG. 11. As shown therein, a patient 151 lying on a table 152 has one of the electrodes 101 placed on his chest and has the other electrode 101 disposed beneath his upper back. The two electrodes 101 are connected to a defibrillator power supply 153 of a conventional type through circuitry consisting of blocks a, b and c which are connected respectively to the portions 106a, 106b and 106c of each of the electrodes 101. The circuitry which is included in the boxes a, b and c is shown in FIG. 12. The components which are in the block a are shown within the dotted rectangle a of FIG. 12, whereas the circuit components in the block b are shown in the dotted rectangle b of FIG. 12. Components identical to the components in the dotted rectangle b are provided in a block c, but are not shown in FIG. 12 because it is merely a repetition of what is shown for block b.

For each of the blocks a, b and c there is provided a current sensing resistor. Thus, in block a, a current sensing resistor R4 is provided, and in block b, a current sensing resistor R5 is provided. Another resistor (not shown) is provided which is similar to the resistor R5 for block c. These current sensing resistors are of very small value, as for example 0.5 ohm so they do not impede normal current flow. This half-ohm resistance is very low compared to the typical body impedance of 100 ohms or more. Thus there is very little energy loss in these resistors R4 and R5, but they still make it possible to measure the currents going through to each of the three portions 106a, 106b and 106c of an electrode 101. Since the amount of current which is to be supplied to each of the portions 106a, 106b and 106c has already been predetermined, programmable unijunction transistors Q1 and Q2 are used to view or sense the voltage which is being developed across the current viewing resistor R4. This is accomplished through a voltage divider consisting of resistors R6 and R7 in block a which determines the voltage developed across the resistor R4 and supplies it to the anodes of the transistors Q1 and Q2. The capacitor C5 across R7 serves to provide a time delay to ensure the stabilization of the gate voltages on Q1 and Q2. If it is ascertained that the current passing through resistor R5 is too low, the voltage that is developed across it is lower than the divided-down voltage from resistor R4 which is on the anode of Q1. The voltage which is developed across the resistor R5 is supplied to the gate of the transistor Q1, and if the anode voltage exceeds by approximately 0.6 volts the gate voltage on the transistor Q1, the programmable unijunction transistor Q1 fires and turns on very rapidly within a microsecond or less and causes the voltage on the anode to appear across the cathode resistor R10, and that voltage is capacitively coupled through a capacitor C4 to the gate of a triac Q4 which is turned on and puts in parallel with the resistor R1 the resistor R3 to reduce the total value of the resistance and thereby increasing the current flow through the resistor R5. Thus it can be seen that the circuitry reacts very rapidly within a few microseconds. This is more than adequate because a typical defibrillation pulse is 4–6 milliseconds in length. The programmable unijunction transistors, as well as the triacs, are very fast-acting devices. Once the triac Q4 fires, it cannot be turned off until the current dissipates. The capacitor C1, which is connected to the gate of Q1, acts as a time delay in conjunction with the resistor R8, and the time delay created by capacitor C2 and resistor R12 are selected so that they are much smaller than the time delay created by capacitor C5 and resistor R7. Thus, by adjusting C1 it is possible to have the circuit react at a certain known time after the defibrillation pulse starts. For example, the gate time delay can be adjusted to provide a time delay of, for example, 5 to 15 microseconds after which the voltage across the viewing resistor can be sensed and the delay caused by capacitor C5 and resistor R7 can be adjusted to 25 to 50 microseconds.

It should be appreciated that a plurality of triacs can be provided with additional resistors of various values so that various values of resistance can be switched in parallel with the resistance R1 of which it is desired to change the overall resistance to achieve the appropriate current flow through a portion of the electrode. Typically, the circuit inserting parallel resistance will start with the highest value resistor to provide the lowest current so that the electrode can be utilized with the lowest impedance patient. If, after triac Q4 turns on and parallels resistor R3 with resistor R1, the current as measured by R5 is still not high enough, PUT Q2 turns "ON" and triggers triac Q3 to turn on, placing R2 in parallel with resistors R3 and R1. This increases the current to electrode segment 106 to nearer the correct value.

With the foregoing circuit it can be seen that the current passing through the center portion 106a is being measured as well as the currents between the center portion and the ring portions 106b and 106c. Thus, for example, two inputs, one from the center portion and another from the ring portion are supplied to a programmable unijunction transistor which is used as a comparator. It determines if the resistance being utilized is adequate or not, and, if not, it fires the appropriate SCR to reduce the value of the resistance in a stepwise fashion. By providing additional sections, it is possible to provide finer steps. From the foregoing, it can be seen that the current which is flowing through the sensing resistor is directly proportional to the impedance of the patient and automatically compensates for this difference in impedance by making appropriate changes in current flow through the various portions of the electrode. Thus it can be seen that this circuitry is particularly efficacious in distributing the current equally into the three portions 106a, 106b and 106c of the electrode to further help to ensure that burning of the patient's skin does not occur during defibrillation. The circuitry should also be helpful in minimizing burning in the event portions of the edge of the electrode are lifted away from the skin of the patient and does not make good contact with the patient. The circuitry would sense such a condition and reduce the current flow to that electrode portion to thereby minimize any possibility of burning of the skin of the patient.

In view of the foregoing, it can be seen that there has been provided a large surface area electrode which makes it possible to control the current distribution in electrodes so that high concentrations of current are avoided to greatly reduce, if not eliminate, undesirable burning which occurs in present day large surface area electrodes. The large surface area electrode of the present invention is for use with a power supply and has a more uniform current density distribution for contacting the exposed surface of the skin of a living body having a contour. The layer of flexible conductive material has first and second surfaces. The layer is normally relatively flat but is capable of assuming the contour of the skin of the body when the electrode is placed in contact with the body with the first surface of the layer of flexible conductive material engaging the exposed surface of the skin of the body. The layer of conductive material is provided with a central portion and a surrounding ring portion with the central portion and the surrounding ring portion having outer margins with edges. Means is provided for forming a flexible backing layer which is secured to the second surface of the layer of flexible conductive material and serves to support the central portion and the surrounding ring portion so that the surrounding ring portion is spaced from and insulated from the central portion. Resistive means is coupled to the central portion and the surrounding portion and is adapted to be coupled to the power supply for controlling the current density at the edges so that the current density does not exceed a predetermined value.

What is claimed is:

1. A large surface area electrode, for use with a power supply having a more uniform current density distribution for contacting an exposed surface of skin of a living body having a contour, comprising a layer of flexible conductive material of a predetermined geometrical shape and having first and second surfaces, said layer of flexible conductive material being normally relatively flat but being capable of assuming the contour of the skin of the body when the electrode is placed in contact with the body with the first surface of the layer engaging the exposed surface of the skin of the body, said layer of flexible conductive material having a central portion and a surrounding ring portion, said central portion and said surrounding ring portion having outer edges, means forming a flexible carrier layer having a first surface secured to the second surface of the layer of flexible conductive material and serving to support said central portion and said surrounding ring portion so that the surrounding ring portion is spaced from and insulated from the central portion and coupling means adapted to couple said central portion and said surrounding ring portion to said power supply for controlling the current densities at said edges so that the current densities at said edges do not exceed predetermined values, said coupling means forming a direct connection to the central portion and including a resistor connected to said surrounding ring portion.

2. An electrode as in claim 1, wherein said layer of flexible conductive material has an additional surrounding ring portion which surrounds said first named surrounding ring portion and wherein said means forming a flexible carrier layer also serves to support the additional surrounding ring portion so that the additional surrounding ring portion is spaced from and insulated from the central portion and the first named surrounding ring portion and wherein said coupling means includes a resistor connected to said additional surrounding ring portion and adapted to be coupled to the power supply.

3. An electrode as in claim 2, wherein said first named surrounding portion has a width and said additional surrounding ring portion has a width which is less than the width of the first named surrounding portion.

4. An electrode as in claim 2, wherein said coupling means includes a conductive flexible foil having portion in contact with said second surface of the layer of flexible conductive material.

5. An electrode as in claim 4, wherein said flexible carrier layer has a second surface together with a flexible backing layer secured to the second surface of the flexible carrier layer, said flexible backing layer being comprises of a resilient flexible material having first and second surfaces, an adhesive adherent to said first surface of the backing layer and also being adherent to the second surface of the carrier layer.

6. An electrode as in claim 5, wherein and backing layer has a size so that it has an outer margin that extends beyond the layer of flexible conductive material.

7. An electrode as in claim 1 together with a release liner removable secured to said first surface of the layer of flexible conductive material and being adherent to the adhesive carried by the outer margin of the flexible carrier layer.

8. An electrode as in claim 7, wherein said resistor is carried by the backing layer.

9. An electrode as in claim 1 together with a non-conductive insulating material disposed in the space between the surrounding ring portion and the central portion.

10. An electrode as in claim 9, wherein said flexible conductive material is formed on a conductive elastomer and wherein the non-conductive insulating material in the space between the surrounding ring portion and the central portion is a non-conductive elastomer.

11. An electrode as in claim 10, wherein said central portion is substantially circular and wherein said surrounding ring portion is in the form of a concentric ring portion.

12. An electrode in claim 1, wherein said flexible conductive material is comprised of a material which is substantially transparent to x-rays.

13. An electrode as in claim 1 having an oval geometric configuration with a longitudinal axis, wherein said means forming a flexible carrier layer includes a tail and further including conductors carried by said tail, said conductors being connected to the central portion and the surrounding portion of the flexible conductive material.

14. An electrode as in claim 13 wherein said tail has a length of at least approximately 6".

15. A large surface area electrode for use with a power supply for contacting an exposed surface of a patient comprising a first conductive element, a second conductive element substantially surrounding the first conductive element and being spaced form the first conductive element, means adapted to connect the first conductive element directly to the power supply and resistor means connected to the second conductive element and being adapted to be connected to the power supply, said resistor means providing a substantially uniform current density in the first and second conductive elements.

16. An electrode as in claim 15 wherein said first and second conductive elements include a flexible conductive metal foil.

17. An electrode as in claim 16 wherein said first and second conductive elements include a flexible conductive material.

18. An electrode as in claim 17 wherein said flexible conductive metal foil has a central portion with radially extending slits therein.

19. An electrode as in claim 18 wherein said flexible metal foil has a central portion having an outer margin, said central portion corresponding in geometry to the first conductive element together with first and second sets of radially extending slits formed in the central portions with one set of slits extending radially outwardly from the center and the other set of slits extending radially inwardly from the outer margin.

20. An electrode as in claim 19 wherein said first and second slits are offset circumferentially with respect to each other.

21. An electrode as in claim 17 wherein said conductive material is a gel.

22. An electrode as in claim 21 wherein said gel has a resistivity of less than 500 ohm-cm.

23. An electrode as in claim 21 wherein said gel is a hydrogel.

24. An electrode as in claim 21 wherein said gel is a conductive elastomer.

25. An electrode as in claim 15 together with a flexible backing material mounting said first and second conductive elements.

26. An electrode as in claim 25 together with a third conductive element having an outer margin, said third conductive element substantially surrounding the second conductive element.

27. An electrode as in claim 26 wherein said first, second and third conductive elements have surface areas which are unequal.

28. An electrode as in claim 27 wherein the surface area of the second conductive element is less than the surface area of the first conductive element and wherein the surface area of the third conductive element is less than the surface area of the second conductive element.

29. An electrode as in claim 26 wherein said conductive elements have surface areas which are approximately equal.

30. An electrode as in claim 26 wherein said backing material has a portion thereof having a perimeter extending beyond the outer margin of the third conductive element, said backing material having circumferentially spaced apart cutouts formed therein which do not intersect the perimeter of the backing material.

31. A large surface area electrode for use with a power supply and adapted to contact the skin of a patent having an impedance, comprising a plurality of separate conductive elements adapted to engage the skin of the patient, and circuitry coupled to the conductive elements and adapted to connect the conductive elements to the power supply for supplying predetermined currents to the conductive elements, said circuitry including viewing resistors for carrying the current supplied to the separate conductive elements, said viewing resistors developing voltages across the same in accordance with the current flowing through the resistors and means coupled to the viewing resistors for ascertaining the voltages developed across the viewing resistors and means responsive to these developed voltages to ascertain whether or not additional current should be supplied to the conductive elements in accordance with the impedance of the skin of the patient.

* * * * *